United States Patent [19]

Rosenberg

[11] 4,197,734

[45] Apr. 15, 1980

[54] APPARATUS FOR DETERMINING BLOOD CLOTTING TIME

[76] Inventor: Alexander Rosenberg, 1000 Edgehill Rd., Roslyn, Pa. 19001

[21] Appl. No.: 928,858

[22] Filed: Jul. 28, 1978

[51] Int. Cl.² ............................................. G01N 33/16
[52] U.S. Cl. ................................... 73/64.1; 23/230 B
[58] Field of Search ...................... 73/64.1, 61.1 C, 54; 346/33 ME; 23/230 B

[56] References Cited

U.S. PATENT DOCUMENTS 2,986,280   5/1961   Magnuson .................... 73/61.1 C X

*Primary Examiner*—Gerald Goldberg
*Assistant Examiner*—Joseph W. Roskos
*Attorney, Agent, or Firm*—Weiser, Stapler & Spivak

[57] ABSTRACT

An apparatus capable of determining the clotting time of blood, without requiring continuous inspection of the sample, is disclosed. The apparatus includes a support frame, which is capable of supporting therein a syringe containing a blood sample, and a turntable adapted to rotate at a known rate of speed. Blood from the syringe drops onto the turntable, the clotting time being automatically and graphically depicted by a chart rotatively carried upon the turntable. The apparatus can also be employed for determining variations in the viscosity of blood plasma and other fluids.

12 Claims, 4 Drawing Figures

APPARATUS FOR DETERMINING BLOOD CLOTTING TIME

BACKGROUND OF THE INVENTION

This invention relates generally to the field of blood testing equipment, and in particular to an apparatus which enables measurement of the clotting time of blood without requiring continuous inspection of the sample.

In the course of various medical treatments, it is often desirable to know the clotting time of the blood of a patient. Also of use is a determination of the sedimentation rate of the blood, as well as the hematocrit, the percentage of solid constituents found in the blood. Previously, the methods of testing for such determinations have required more or less continuous, or at least periodic, inspection of the sample, examples of such prior art methods being the Lee-White Method or the Capillary Tube Method.

The more or less continuous inspection required by the above methods has the effect of requiring the expenditure, by trained personnel, of an undue amount of time in obtaining the desired data. This results in both the need for increased personnel to properly staff a testing facility as well as increased costs for such tests due to the labor required to perform them. It is therefore desirable to remove the need for the personal attendance of trained personnel during the performance of such tests, thereby reducing labor and medical costs.

SUMMARY OF THE INVENTION

This invention relates generally to the field of medical testing equipment, and in particular to an apparatus which enables the clotting time of blood to be measured automatically, without requiring the attendance of trained personnel during the testing process.

In accordance with usual practice, when it is desired to test a patient's blood, a sample of blood is removed using a syringe which is generally conventional in appearance and use. In the present invention, the same syringe, after being filled with the blood sample, is inserted into an apparatus having a frame which is capable of supporting the syringe over a rotatable table. The table rotates at a preselected, known rate of speed beneath the syringe.

The syringe is provided with an air passage to its interior which acts as a vent and enables blood from the syringe to drop onto the turntable drop by drop. The opening in the syringe needle is small enough to deposit droplets of blood on the turntable which are sufficiently small to form spots of uniform, relatively small size. These droplets continue as the turntable rotates beneath the syringe, until such time as the blood exhibits clotting, or just before that point in time. It is then possible, at the convenience of the technician, to calculate the clotting time by determining the degrees of rotation of the turntable during the time interval between the first droplet of blood and the last droplet of blood.

The apparatus can also be used for determining variations in viscosity of blood plasma and other fluids.

The relationship between clotting time and the degrees of rotation of the turntable may be determined using any one of several methods. For example, by using a graph upon the turntable having spaced markings which translate rotation directly into time, clotting time may be read directly from the graph. This measurement may also be made by determining the rotational distance or movement travelled by the turntable, and, knowing the rate of speed of rotation, calculating the time required to traverse such rotational distance between the first and last drops deposited on the turntable.

In this manner, the clotting time of blood may be determined automatically, without the constant or periodic attendance of trained personnel. All that is required is a minimal set up period, and examination of the results of the test at any time after it has been completed. Such a method therefore serves to free trained personnel to perform more intricate tests or duties, in addition to providing the technician with a fixed recording of the results which may be used for subsequent verification of the data obtained. Moreover, by providing a uniform measuring technique, accuracy of the resulting measurement can be improved.

It is therefore an object of the present invention to provide an improved apparatus which is capable of measuring the clotting time of blood.

It is another object of the present invention to provide an apparatus which is capable of measuring the clotting time of blood automatically, without requiring continuous inspection by trained personnel.

It is another object of the present invention to provide an apparatus which is capable of automatically measuring the clotting time of blood, and which also provides a permanent recording of the test results.

It is another object of the present invention to provide an apparatus which is capable of measuring the clotting time of blood which provides uniform and accurate results.

It is another object of the present invention to provide an apparatus which is capable of automatically measuring the clotting time of blood which is simple in construction, inexpensive to manufacture and easy to use.

These objects and others will become apparent to those skilled in the art from the following disclosure of the preferred embodiment of the invention taken in conjunction with the drawings provided in which like reference characters refer to similar parts throughout the several views, in which:

DESCRIPTION OF THE PREFERRED EMBODIMENT OF THE INVENTION

Figure 1:
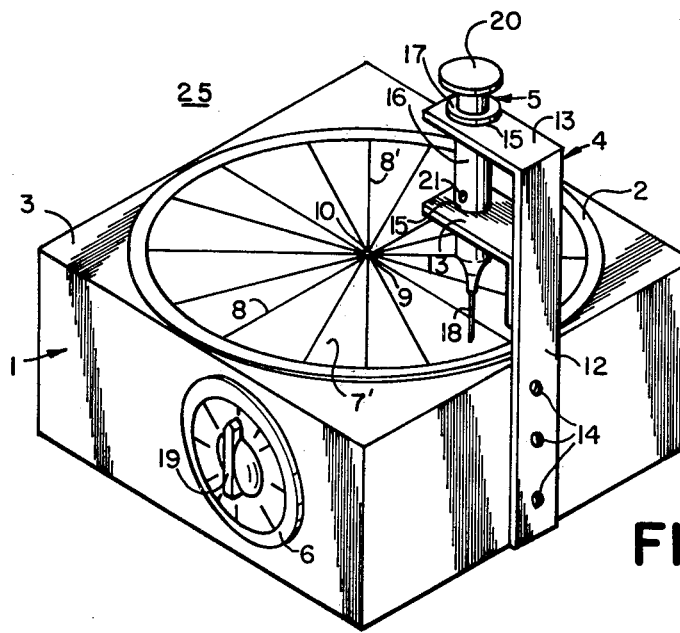
FIG. 1 is an isometric view of an apparatus useful in determining the clotting time of blood as it would appear during use.

Although specific terms are used in the following description for the sake of clarity, these terms are intended to refer only to the particular structure of the invention selected for illustration in the drawings, and are not intended to define or limit the scope of the invention.

Referring now to the drawings, there is shown in FIG. 1 a preferred embodiment of an apparatus 25 which is capable of determining the clotting time of blood. The apparatus 25 comprises generally a base 1, the top 3 of the base 1 being provided with a turntable 2. A frame 4 is connected to the base 1 and is adapted to support a syringe 5 over the turntable 2.

The base 1 may be any shape which can define a cavity sufficiently large to house the mechanism (not shown) which rotationally drives the turntable 2. While the base 1 is illustrated in rectangular configuration, it will be appreciated that other shapes are clearly possible. The base 1 may be formed of metal, plastic or other suitable material, and primarily serves as a housing for the remaining components of the apparatus.

Figure 2:
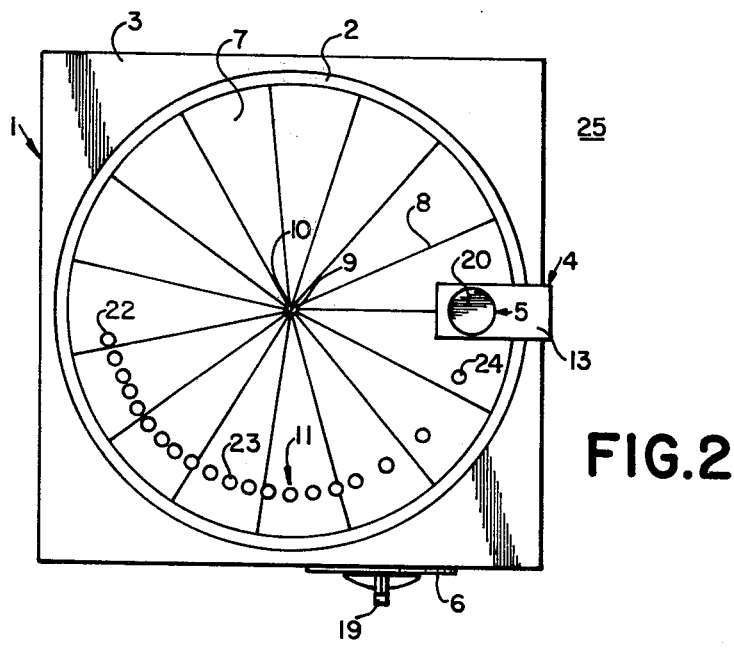
FIG. 2 is a top plan view of the apparatus, during use, showing the pattern of drops of blood produced during operation and having a removable recording chart on the turntable to receive the pattern.

The turntable 2 is rotatable at the top of the base by a drive mechanism (not shown) which is preferably connected to a timer 6, for the purpose more fully described below. As best seen in FIG. 2, the turntable 2 comprises a flat, plate-like structure which may be mounted on the top 3 of the base, by employing bearings, bushings or other construction to facilitate turntable rotation. The turntable 2 is preferably constructed of rubber, plastic or metal, and a non-slippery surface is preferably provided to assure accurate, non-slip rotation of a recording or chart graph 7 to be placed thereon.

A recording chart 7 is placed on top of the turntable 2 to provide a record of the blood clotting time test. The recording chart 7 is circular and is preferably formed of paper or other inexpensive planar material. Use of such a chart 7 for each separate test enables the drops of blood to be permanently recorded and preserved for later use. The recording chart 7 is preferably provided with uniformly spaced markings 8, radially extending from the center, which may be used to calculate the clotting time of the blood. A hole 9 is provided at the center of the recording chart 7 which is capable of being engaged by a dowel 10 located at the center of the turntable 2. The hole 9 and dowel 10 are shown which combine to securely retain the recording chart 7 in place, however other suitable elements may be employed. For example, such retention can also be provided by a raised lip (not shown) surrounding the turntable 2, which could be adapted to engage the periphery of the recording chart 7 to retain it in position.

If desired, the turntable 2 as illustrated could be replaced by a linearly moving platen suitable to support a strip chart type of recorder (not shown) which provides linearly recorded patterns as opposed to the circular droplet pattern illustrated in FIG. 2. In such case the time interval markings would extend transversely in spaced arrangement along the strip chart rather than radially.

Referring now to FIG. 1, it will be observed that the base 1 supports a frame 4 which extends upwardly from the base and cantilevers over the top 3 and the turntable 2. The frame 4 has a vertical section or support 12, the top end of which is provided with at least one, and preferably with two, horizontal support members 13. The frame 4 may be connected to either the top or side of the base 1 using any of several known fastening means, for example the screws 14 as illustrated. In this embodiment, the turntable itself forms a recording surface 7' which is subdivided into segments by the circularly spaced, radially extending, calibration lines 8'.

The horizontal support members 13 are provided respectively with registered openings 15 sufficiently large to frictionally, slidingly engage the outer periphery of the barrel 16 of a syringe 5. In this manner, the syringe 5 may be inserted, in an inverted orientation, into the openings 15, until further travel is limited by a flanged portion 17 provided as part of the syringe 5. In this manner, the syringe 5 can be supported over the turntable 2 with the needle 18 facing downwardly toward the turntable 2.

In operation, the turntable 2 is set in motion, preferably prior to insertion of the syringe 5 into the openings 15 of the frame 4. Initiation of motion may be accomplished by starting a motor, either electrical or mechanical which is operatively connected to the turntable 2. Such a motor should be constant speed and may advantageously be part of a timer 6, either electrical or mechanical, and is controlled by an externally mounted control knob 19. In this manner, operation of the timer 6 initiates operation of the apparatus 25 and also provides a time reference for the operator or technician.

A blood sample is conventionally withdrawn from a patient using a syringe 5 in known manner. The syringe 5 used for this purpose has a needle 18, affixed to the end of a barrel 16, into which is inserted a plunger 20, in conventional manner. The syringe 5 containing the blood sample is then inserted into the registered openings 15 provided in the support members 13 of the frame 4, the barrel 16 of the syringe frictionally slidingly engaging the openings 15, until downward movement is stopped by the flange 17 of the syringe 5.

Blood from the syringe 5 is then permitted to drop by gravity from the needle 18 onto the recording chart 7 or turntable recording surface 7' in discrete droplets. To allow this, a small vent or air passage 21 is provided through the barrel 16 of the syringe 5. The air passage 21 is spaced sufficiently far from the needle end of the syringe 5, so as not to interfere with the formation of the vacuum required for aspiration of blood into the syringe 5. Further retraction of the plunger 20 rearwardly within the barrel 16 exposes the air passage 21 to the needle 18 which permits blood to exit the syringe 5. Should a syringe be used that does not have such an air passage 21, it is still possible to initiate the drop by drop operation by removing the plunger 20 from the barrel 16.

FIG. 2 illustrates the arcuate pattern or track 11 that results as a consequence of rotation of the turntable 2. A first spot or droplet of blood 22, represents the starting point in the testing procedure. As the turntable 2 rotates uniformly at a known rate, successive droplets from the syringe result in formation of the pattern 11. The individual drops forming the track or pattern 11 are limited in size, thus forming uniform and discrete spots 23 on the recording chart 7. The size of each spot 23 is limited by the size of the droplets of blood exiting the syringe 5.

As the test procedure continues and time passes, the viscosity of the blood in the sample will increase, eventually reaching a point where clotting will occur. This results in an increasingly slower rate of droplet fall causing the spots 23 to be spaced further and further apart along the circular path until such time as full clotting occurs, or actually just before that time, at which point the pattern stops, for example at 24. At this point, the track or pattern 11 defined by end points 22, 24 represents the clotting time of the sample found in the syringe 5. By counting the markings 8, which markings represent time intervals, the time period can be easily determined.

It will be noted that, after the initial set up procedure, the measurement of clotting time is accomplished without requiring intervention or inspection by a technician or operator. Moreover, there is no need for an operator to return to the apparatus 25 immediately after completion of the test. The turntable 2 may continue to rotate, but after clotting, no additional blood droplets will fall from the syringe 5, thereby preserving the test results upon the graph or chart 7 until such time as the operator can return to the apparatus 25 to interpret the test results. Use of the timer 6 to operate the turntable 2 is helpful to enable an operator to limit operation of the unattended apparatus 25, so that it need not run continuously until the operator can return to manually shut down the device.

At the convenience of the technician, the recording chart 7 may be removed from the turntable 2 and the clotting time may be determined. By providing radially spaced markings 8, 8' on the recording chart 7 or recording surface 7', it is possible to calibrate the turntable surface 7' and recording chart 7, thereby translating rotational distance directly into time. A simple reading of the clotting time, directly from the recording chart 7, based upon the length of the track 11, is thus permitted. In addition, the recording chart 7, being removable from the turntable 2, provides the technician with a fixed recording of the test results, whih may be referred to subsequently for verification of the test data.

In this manner the clotting time of blood may be determined accurately, simply, and without the constant attention of an operator. It will, of course, be understood that many variations of the above apparatus are possible.

For example, the circular turntable 2 and recording chart 7 may be replaced with a strip chart type recorder, as previously mentioned. In this case, the track formed by the individual droplets from the syringe 5 would be linear rather than arcuate or circular, however operation would be essentially similar to that previously described. Interpretation of the test results could be similarly performed using calibrated markings which extend transversely along the strip chart in longitudinally spaced intervals.

Figure 3:
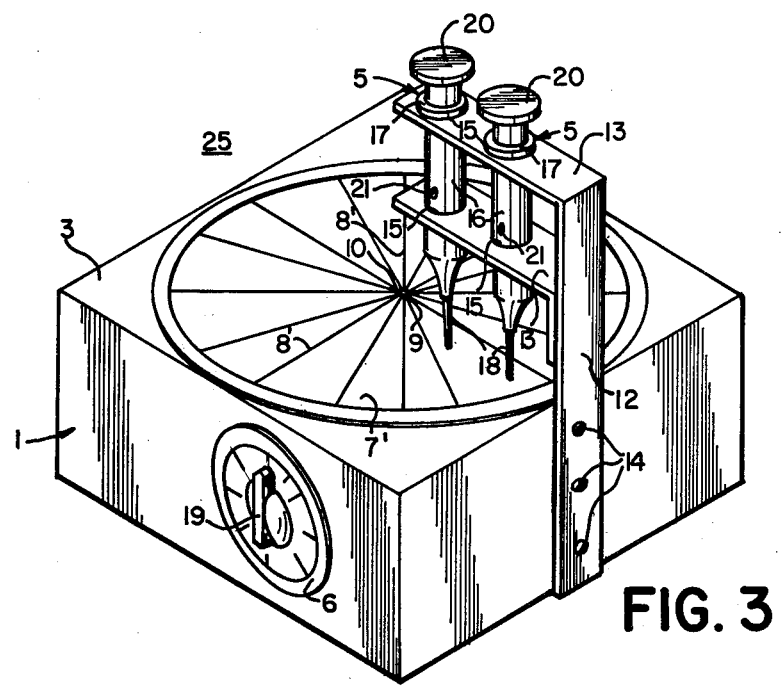
FIG. 3 is an isometric view similar to FIG. 1 showing a modified frame supporting a pair of syringes.
Figure 4:
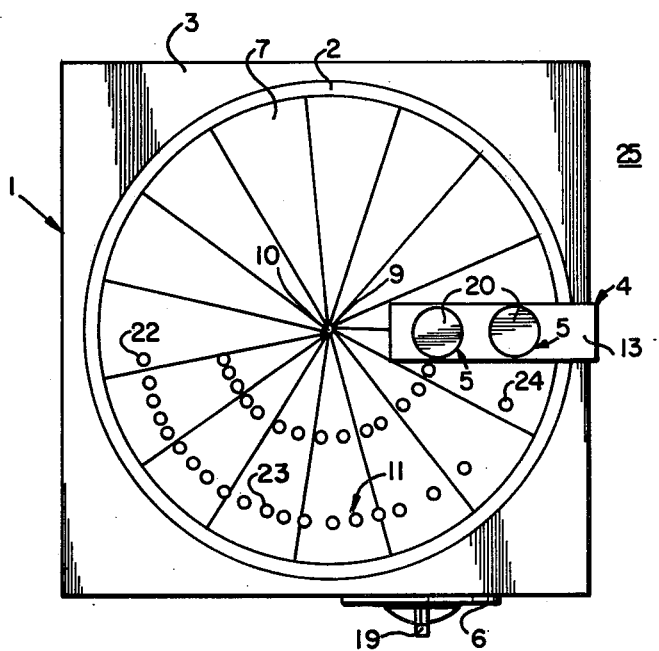
FIG. 4 is a top plan view of the apparatus of FIG. 3.

It is also possible to modify the frame 4 to provide further versatility to the above described apparatus 25. The frame 4 as illustrated is capable of supporting but a single syringe 5 therein. However, by extending the support members 13 and providing additional pairs of registered openings 15 in the support members 13, it is possible to retain a plurality of syringes 5, in series, within a single frame 4 (see FIGS. 3 and 4). Additional frames 4 may be provided at other locations peripherally spaced about the base 1 to provide additional, parallel, testing stations. In this manner a multiplicity of samples may be tested simultaneously, the number being limited only by space on the recording chart. The frame 4 is illustrated as perpendicular to the base 1 and top 3, however other angular positions are possible, and such angular position may be made adjustable if desired. This may be readily accomplished by replacing the plurality of fasteners 14 with a pivotal type of connector, for example a single thumb screw. In this manner, the frame could be pivoted about the thumb screw to a desired angular position relative to the base and then secured in that position by conventionally tightening the thumb screw.

Although the turntable 2 is preferably provided with a removable recording chart 7, such an element is not required for operation. The droplets of blood may also be permitted to drop directly onto the turntable surface 7', which may, if desired, be provided with integral markings 8' useful in directly determining clotting time from the resulting track or pattern of blood. In such case, a washable surface, such as plastic or metal would be preferable.

It may therefore be seen that the above disclosed invention serves well to accomplish the objects previously stated. It may also be seen that the above described invention may be embodied in other specific forms in addition to those above disclosed and therefore the disclosure made should be interpreted in an illustrative and not a limiting sense.

What is claimed is:

1. An apparatus for determining the change in viscosity of a fluid which comprises
   a base;
   a means for retaining a syringe adapted to contain a fluid sample to support the syringe over the base;
   a recording means for recording drops of fluid which drop from the syringe, the recording means being rotatably carried on the base and beneath the syringe;
   the retaining means comprising a frame extending upwardly from the base and being cantilevered over the recording means,
   the frame having at least one support member which is adapted to retain the syringe; and
   the support member comprising plural means to retain a plurality of syringes over the recording means.

2. The apparatus of claim 1 and means to adjust the angle of the frame with respect to the base.

3. An apparatus for determining the change in viscosity of a fluid which comprises
   a base;
   a means for retaining a syringe adapted to contain a fluid sample to support the syringe over the base;
   a recording means for recording drops of fluid which drop from the syringe, the recording means being rotatably carried on the base and beneath the syringe; and
   the syringe comprising a cylindrical sidewall defining a hollow body, a needle positioned at one end and being in fluid communication with the hollow body, a plunger reciprocal above the needle and an air passage through the sidewall in communication with the hollow interior of the syringe.

4. The apparatus of claim 3 wherein the air passage is positioned at a point sufficiently far away from the end of the syringe containing the needle to permit aspiration of a fluid sample into the syringe, the plunger being adapted to be pulled through the hollow body sufficiently to permit fluid communication between the needle and the air passage whereby the air passage can act as a vent to permit the fluid to exit the syringe through the needle in the form of discrete droplets.

5. An apparatus for determining the change in viscosity of a fluid which comprises
   a base;
   a means for retaining a syringe adapted to contain a fluid sample to support the syringe over the base,
   a recording means for recording drops of fluid which drop from the syringe, the recording means being rotatably carried on the base and beneath the syringe,
   the recording means being a turntable, the turntable being rotationally mounted on the base, which turntable is capable of rotation beneath the syringe; and the turntable comprising radially extending calibration lines which divide the turntable into segments.

6. An apparatus for determining the change in viscosity of a fluid which comprises a base;

a means for retaining a syringe adapted to contain a fluid sample over the base:

a recording means for recording drops of fluid which drop from the syringe, the recording means being rotatably carried on the base and beneath the syringe, the recording means comprising a turntable, the turntable being rotationally mounted on the base, the turntable being capable of rotation beneath the syringe; and a removable recording chart placed on top of the turntable, said chart being positioned beneath the syringe whereby droplets of fluid from the syringe can fall upon the chart, the recording chart having radially extending calibration lines which divide the turntable into segments.

7. The apparatus of claim 5 or 6 wherein the calibration lines are calibrated according to time.

8. A method for determining the clotting time of blood using an apparatus comprising a base, a means for retaining a syringe containing a blood sample over the base, and a means for recording drops of blood which drop from the syringe, which is positioned beneath the syringe, which method comprises placing a syringe containing a blood sample in the means for retaining a syringe;

dropping blood droplets from the syringe onto the recording means; while concurrently moving the recording means beneath the syringe; and determining, from the resulting pattern of droplets of blood upon the recording means the clotting time of the blood sample, whereby blood clotting time may be determined without the continuous or periodic inspection of the sample by an operator.

9. The method of claim 8 wherein the recording means rotates beneath the syringe.

10. The method of claim 9 wherein the recording means rotates at a known and constant rate.

11. The method of claim 8 further comprising regulating movement of the recording means using a timer which determines the points at which movement of the recording means starts and ends.

12. The method of claim 8 wherein the determination of clotting time is accomplished by reading clotting time directly from the recording means, the recording means being calibrated according to time, the reading depending upon the length of a pattern of droplets of blood dropped upon the recording means.

* * * * *